| United States Patent [19] | [11] 3,989,703 |
|---|---|
| Niculescu-Duvăz et al. | [45] Nov. 2, 1976 |

[54] PROCESS OF PREPARING N[P-{[(2,4-DIAMINO-6-PTERIDYL)-METHYL]N$^{10}$-METHYLAMINO}-BENZOYL]-GLUTAMIC ACID

[75] Inventors: Ion Niculescu-Duvăz; Liviu Valentin Feyns; Dan Suster; Gheorghe Ciustea, all of Bucharest, Romania

[73] Assignee: Institutul Oncologic, Bucharest, Romania

[22] Filed: Mar. 22, 1974

[21] Appl. No.: 453,914

[52] U.S. Cl. .............................. 260/251.5; 424/251
[51] Int. Cl.$^2$ ........................................ C07D 475/08
[58] Field of Search .................................. 260/251.5

[56] References Cited
UNITED STATES PATENTS

| 2,561,658 | 7/1951 | Gardner et al. .................. 260/251.5 |
| 2,667,485 | 1/1954 | Petering ........................... 260/251.5 |

*Primary Examiner*—Nicholas S. Rizzo
*Assistant Examiner*—Jose Tovar
*Attorney, Agent, or Firm*—Ladas, Parry, Von Gehr, Goldsmith & Deschamps

[57] ABSTRACT

A three-step process is provided for preparing the L,D and DL isomers of N[p-{[(2,4-diamino-6-pteridyl)-methyl]N$^{10}$-methylamino }-benzoyl]-glutamic acid. The first step produces: 2,4-diamino-6-hydroxymethyl pteridine by condensation in a buffered aqueous media of 2,3,4,5-tetraminopyrimidine dihydrochloride with the bisulphite addition product of 1,3-dihydroxyacetone in the presence of cysteine as catalyst and using selenium dioxide and a continuous air bubbling as oxidation agents. In the next step, 2,4-diamino-6-halomethylpteridine is obtained by halogenation of the previously obtained 2,4-diamino-6-hydroxymethylpteridine in an inert media with a halogenation agent such as thionyl chloride, in the presence of a basic catalyst such as pyridine or triethylamine. In the third step, N[p-{[(2,4-diamino-6-pteridyl)-methyl]-N$^{10}$-methylamino}-benzoyl-]-glutamic acid is produced by condensation of the 2,4-diamino-6-halomethylpteridine with N[p-(N-methylamino)-benzoyl]-glutamic acid at pH 3–4 in an aqueous buffered solution.

2 Claims, No Drawings

PROCESS OF PREPARING N[P-{[(2,4-DIAMINO-6-PTERIDYL)-METHYL]N[10]-METHYLAMINO}-BENZOYL]-GLUTAMIC ACID

The present invention relates to a novel process of preparing N[p-{[(2,4-diamino-6-pteridyl)-methyl]-N[10]-methylamino}-benzoyl]-glutamic acid of the formula:

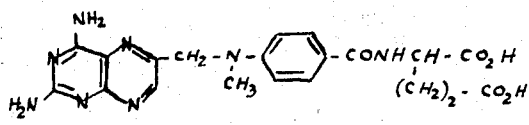

(I)

This compound is largely used in cancer chemotherapy.

It is known in the art that N[p-{[(2,4-diamino-6-pteridyl) methyl]-N[10] methylamino}-benzoyl]-glutamic acid can be prepared by one step procedures involving the condensation of a 2,4,5,6-tetraaminopyrimidine salt and of N[p-(N-methylamino)-benzoyl]-glutamic acid either with a 1,2-dihalo-propionaldehyde or with a 1,1,3-trihaloacetone.

The main disadvantage of the procedure using a 1,2-dihalopropionaldehyde is the poor yield and the formation of a crude product with a low content of (I). The purification of this crude product is very difficult and leads to large losses of (I). No data are available in the art concerning the total yield obtained by this procedure, but we have found that a 1–2% yield (based on N[p-(N-methylamino)-benzoyl]-glutamic acid) of a crude product containing 35% (I) was obtained by this procedure.

The procedure using 1,1,3-trichloracetone was found by us to result in the formation of a mixture of two isomers, namely N[p-{[(2,4-diamino-6-pteridyl)-methyl]-N[10] methylamino}-benzoyl]-glutamic acid (I) and N[p-{[(2,4-diamino-7-pteridyl)-methyl]-N[10]methylamino}-benzoyl]-glutamic acid, in which only (I) is biologically active. No literature data and no suitable method for the separation of these two isomers were found.

The main disadvantage in the literature methods for the preparation of 2,4-diamino-6-hydroxymethylpteridine is the necessity to use a pure 1,3-dihydroxyacetone, free of methyl-glyoxal, which affords by condensation a considerable yield of 2,4-diamino-6-methylpteridine. Purification of 1,3-dihydroxyacetone is rather difficult, especially the final distillation under high vacuum.

The procedure according to the present invention avoids the above mentioned disadvantages by preparing the L, D or DL isomers of (I) by a three step process, namely:

1. Synthesis of 2,4-diamino-6-hydroxymethylpteridine by condensation in a buffered aqueous media (alkaline acetates are preferred) of a 2,4,5,6-tetraaminopyrimidine dihydrochloride with the bisulphite addition product of 1,3-dihydroxyacetone, in the presence of cysteine as catalyst, and using selenium dioxide and a continuous air bubbling as oxidizing agents. The reaction may be carried out at a pH from 3 to 7.5 and a temperature from 20° to 100° C.

2. Halogenation, for example by thionyl chloride, of the previously obtained 2,4-diamino-6-hydroxymethylpteridine in an inert organic medium (i.e. chloroform, methylene chloride etc.) in the presence of a basic catalyst (i.e. pyridine, triethylamine, etc.) to produce 2,4-diamino-6-halomethylpteridine. The molar ratio of pteridine derivative: thionyl chloride may be between 0.2 and 1.2 and the pteridine derivative may be present in 1.0 – 10.0 parts by weight for each part of basic catalyst.

3. Synthesis of N[p-{[(2,4-diamino-6-pteridyl)-methyl]-N[10]-methylamino}-benzoyl]-glutamic acid by condensation of the crude 2,4-diamino-6-halomethylpteridine obtained in the previous step with N[p-(N-methylamino)-benzoyl]-glutamic acid at a pH of 3–6 in an aqueous buffered solution. The temperature may be between 20° and 100° C and preferably is gradually increased over a reaction time of up to about 50 hours. The purification of the crude reaction product, accomplished by usual methods described in the literature for this type of compound, gave a total yield of 10 – 15% based on N[p-(N-methylamino)-benzoyl]-glutamic acid. The product of this purification contained 95% of compound (I), determined by paper chromatography and UV spectroscopy and was free of the 7-isomer.

The following example is included in order to illustrate the present invention:

1. 2,4-DIAMINO-6-HYDROXYMETHYLPTERIDINE

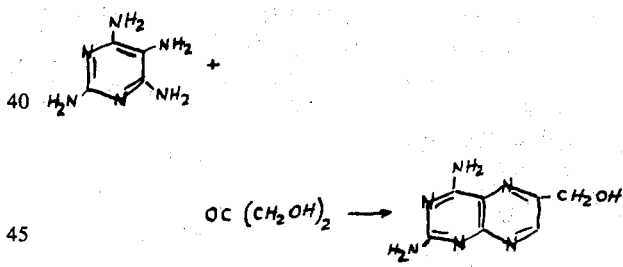

A solution of 6.4 grams of barium chloride in a minimum amount of hot water was added with stirring at a temperature of 70°–80° C to a suspension of 7.6 grams of 2,4,5,6-tetraaminopyrimidine sulphate in 104 ml water. The resulting suspension was stirred for 30 minutes and the formed barium sulphate was removed by filtration and washed on the funnel with 26 ml water at a temperature of 70° C. The solution containing the 2,4,5,6-tetraaminopyrimidine dihydrochloride is diluted with water to a final volume of 400 ml.

A solution of 128 grams of sodium acetate, 136 grams of bisulphite addition product of 1,3-dihydroxyacetone (free of methyl glyoxal) and 46 grams of cysteine hydrochloride in 390 ml water was prepared at room temperature in a 2 liter three-necked flask fitted with a stirrer, an air-bubbling system and a dropping funnel. To this solution, the 400 ml of the previously prepared solution of 2,4,5,6-tetraaminopyrimidine dihydrochloride were added with energic stirring and air-bubbling. A solution of 8 g of selenium dioxide dissolved in the minimum amount of water was made.

Half of this solution was added to the reaction mixture immediately after the addition of the tetraaminopyrimidine solution and the other half 4–7 hours later.

The reaction was allowed to proceed for 24 hours at room temperature.

The reaction can be carried out in a similar manner in a range of temperatures from 20° to 100° C, but the yield is lower. After the end of the reaction, the solution is kept 1 hour at 4° C. The precipitate was filtered off, washed on the funnel with cold alcohol, alcohol-:ethyl ether (1:1) and ethyl ether, then dried under vacuum for 24 hours at 50°. The yield is 3,8 g (72%) of 2,4-diamino-6-hydroxymethylpteridine.

2. 2,4-DIAMINO-6-CHLOROMETHYLPTERIDINE.

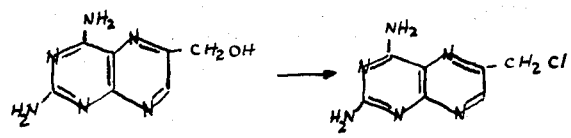

In a round bottomed flask equipped with stirrer and reflux condenser, 7 g of dry and finely powdered 2,4-diamino-6-hydroxymethylpteridine were suspended in 175 ml of anhydrous chloroform. Then, 2.1 ml of anhydrous pyridine and 14 ml of thionyl chloride were added. The reaction mixture was kept for one hour under gentle reflux and efficient stirring.

After cooling, the precipitate was filtered, washed with anhydrous chloroform and dried on the funnel.

A yield of 8.6 grams of crude 2,4-diamino-6-chloromethylpteridine was obtained.

3. N[p-{[(2,4-DIAMINO-6-PTERIDYL)-METHYL]-$N^{10}$ METHYLAMINO}-BENZOYL]-GLUTAMIC ACID.

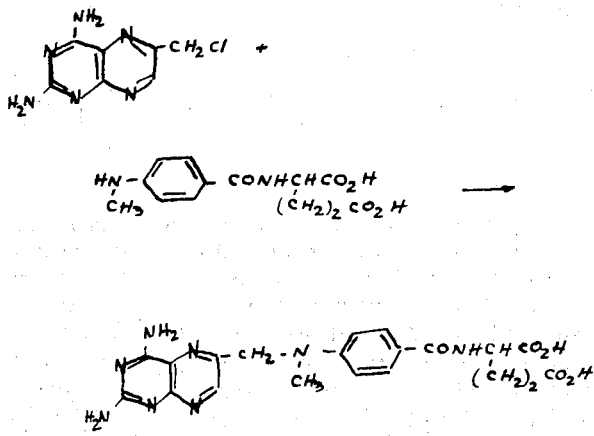

In a 500 ml three-necked round bottomed flask fitted with a stirrer, a dropping funnel and a reflux condenser, a solution of 20 grams of sodium acetate in 250 ml of water was prepared. The pH of the solution was adjusted to 4 with 1 N hydrochloric acid. To this solution 2.8 grams of N[p-(N-methylamino)-benzoyl]-L-glutamic acid was added with efficient stirring and then, over a period of 1 hour, a solution of 2 grams of 2,4-diamino-6-chloromethylpteridine in 15 ml concentrated formic acid was added. The pH of the reaction mixture was maintained at 4.0.

The reaction mixture was kept for 40 hours at 45° C, then the temperature was raised to 55° C for 2 hours, then to 65° C for 2 hours, and finally to 75° C for 1 hour.

The precipitate was filtered off and suspended in 150 ml of sodium carbonate solution having a pH of 11 – 12. The suspension was heated to 60° C and the pH adjusted to 11 – 12 with sodium carbonate. The solution was filtered and the filtrate was adjusted to pH 7 with 1 N HCl and cooled to 4° C for 24 hours.

After treatment with active charcoal and stirring over a period of 15 minutes, the solution was filtered, brought to pH 4 with 1 N HCl and allowed to stand overnight at 4° C.

The precipitate was filtered off, washed with 10 ml of cold water and with an equal volume of cold ethanol, and then was dried at 50° C for 24 hours under vacuum. The crude product was obtained in an amount of 1.3 grams containing about 60% N[p-{[(2,4-diamino-6-pteridyl)-methyl]-$N^{10}$-methylamino}-benzoyl]-L-glutamic acid (as determined by chromatography and spectrophotometry).

Further purification of the crude product is accomplished by usual chromatographic methods gave a total yield of 10–15% N[p-{[(2,4-diamino-6-pteridyl)-methyl]-$N^{10}$ methylamino}-benzoyl-]L-glutamic acid of at least 95% purity.

By the same procedure, and under the same conditions the D and DL isomers were prepared using in the final step N[p-(N-methylamino)-benzoyl-]-D or DL-glutamic acid.

What is claimed is:

1. A process for preparing N[p-{[(2,4-diamino-6-pteridyl)-methyl]-$N^{10}$-methylamino}-benzoyl]L-, D- or DL-glutamic acid which comprises (1) reacting at a pH within the range of 3 and 7.5 and at a temperature range between 20° and 100° C, 2,4,5,6-tetraaminopyrimidine dihydrochloride with the bisulphite addition product of 1,3-dihydroxyacetone, the molar ratio between said dihydrochloride compound and said bisulphite addition product being in the range between 0.2:1 and 1:1, in aqueous medium using air bubbling and selenium dioxide as oxidation agents and cysteine as catalyst to form 2,4-diamino-6-hydroxymethyl pteridine; (2) halogenating the last mentioned compound with thionyl chloride in an inert organic medium selected from the group consisting of chloroform and methylene chloride, in the presence of a basic catalyst selected from the group consisting of pyridine and triethylamine, the molar ratio of pteridine derivative to thionyl chloride being in the range between 0.2:1 and 1.2:1, and the pteridine derivative being present in 1.0–10.0 parts by weight for each part of said basic catalyst, the reaction being carried out at the reflux temperature of the inert medium used, to form 2,4-diamino-6-chloromethyl-pteridine; and (3) condensing the latter with N[p-(N-methylamino) benzoyl]-L,D-or DL-glutamic acid in a buffered aqueous medium, at a pH in the range of 3.0 to 6.0 and at a temperature between 20° and 100° C.

2. The process according to claim 1, wherein in step (3) the temperature is gradually increased over a reaction time of up to about 50 hours.

* * * * *